(12) United States Patent
Hoshishima et al.

(10) Patent No.: US 8,817,244 B2
(45) Date of Patent: Aug. 26, 2014

(54) FLUORESCENCE MEASUREMENT DEVICE AND FLUORESCENCE MEASUREMENT METHOD

(75) Inventors: Kazuteru Hoshishima, Tamano (JP); Shigeyuki Nakada, Tamano (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 167 days.

(21) Appl. No.: 13/521,684

(22) PCT Filed: Jan. 13, 2011

(86) PCT No.: PCT/JP2011/000115
§ 371 (c)(1),
(2), (4) Date: Jul. 11, 2012

(87) PCT Pub. No.: WO2011/086913
PCT Pub. Date: Jul. 21, 2011

(65) Prior Publication Data
US 2012/0281204 A1 Nov. 8, 2012

(30) Foreign Application Priority Data
Jan. 15, 2010 (JP) .................. 2010-006406

(51) Int. Cl.
| | | |
|---|---|---|
| G01N 21/00 | (2006.01) | |
| G01N 21/53 | (2006.01) | |
| G01J 3/02 | (2006.01) | |
| G01N 21/64 | (2006.01) | |
| G01N 15/14 | (2006.01) | |

(52) U.S. Cl.
CPC . *G01J 3/02* (2013.01); *G01N 21/53* (2013.01); *G01N 15/1459* (2013.01); *G01N 15/1429* (2013.01); *G01N 21/645* (2013.01); *G01N 2021/6491* (2013.01)
USPC .......................................................... 356/73

(58) Field of Classification Search
CPC ............... G01J 3/02; G01J 3/513; G01J 3/51; G01N 15/1459; G01N 21/65
USPC ............................................................ 356/73
See application file for complete search history.

(56) References Cited

U.S. PATENT DOCUMENTS

| | | |
|---|---|---|
| 2009/0230308 A1 | 9/2009 | Kimura |
| 2009/0242802 A1 | 10/2009 | Kimura |
| 2010/0314557 A1 | 12/2010 | Hayashi et al. |

FOREIGN PATENT DOCUMENTS

| | | |
|---|---|---|
| EP | 2 251 672 A1 | 11/2010 |
| JP | 62-278436 | 12/1987 |

(Continued)

OTHER PUBLICATIONS

International Search Report of corresponding International Application No. PCT/JP2011/000115, dated on Apr. 5, 2011.

(Continued)

*Primary Examiner* — Tarifur Chowdhury
*Assistant Examiner* — Md Rahman
(74) *Attorney, Agent, or Firm* — Global IP Counselors, LLP (57) ABSTRACT

Disclosed herein is a fluorescence measuring apparatus capable of more accurately measuring fluorescence emitted when an object to be measured is irradiated with laser light. The apparatus for measuring fluorescence emitted when an object to be measured is irradiated with laser light includes: a laser light source that irradiates the object to be measured with laser light; a first light-receiving unit that receives scattered light emitted when the object to be measured is irradiated with the laser light; a second light-receiving unit that receives fluorescence emitted when the object to be measured is irradiated with the laser light; and a signal processing unit that assigns a weight to a signal of the fluorescence received by the second light-receiving unit depending on an intensity of the scattered light received by the first light-receiving unit.

8 Claims, 11 Drawing Sheets

(56) References Cited

FOREIGN PATENT DOCUMENTS

| | | |
|---|---|---|
| JP | 2007-101397 A | 4/2007 |
| JP | 2009-216532 A | 9/2009 |
| JP | 2009-244018 A | 10/2009 |
| JP | 2009-244080 A | 10/2009 |
| WO | WO-2009/098868 A1 | 8/2009 |
| WO | WO-2009/110314 A1 | 9/2009 |

OTHER PUBLICATIONS

Shigeyuki Tanaka et al., "Development of fluorescence lifetime FRET flow cytometer", Mitsui Zosen Technical Review, Mar. 31, 2007, No. 190, pp. 54 to 60.

FLUORESCENCE MEASUREMENT DEVICE AND FLUORESCENCE MEASUREMENT METHOD

TECHNICAL FIELD

The present invention relates to an apparatus and a method for measuring fluorescence emitted when an object to be measured is irradiated with laser light.

BACKGROUND ART

A fluorescence measuring apparatus is known which acquires information about an object to be measured by irradiating the object to be measured with laser light and receiving fluorescence emitted from the object to be measured.

A flow cytometer using such a fluorescence measuring apparatus can acquire information per object to be measured by allowing objects to be measured such as cells, DNAs, RNAs, enzymes, or proteins labeled with a fluorochrome to flow in a sheath fluid, irradiating the object to be measured with laser light, and measuring fluorescence emitted from the fluorochrome labeling the object to be measured.

Further, another fluorescence measuring apparatus is known which acquires a fluorescence relaxation time constant by irradiating an object to be measured with laser light and receiving fluorescence emitted from the object to be measured (Patent Document 1).

CITATION LIST

Patent Document

Patent Document 1: JP-A-2007-101397

SUMMARY OF INVENTION

Technical Problem

When a fluorescence measuring apparatus that receives fluorescence emitted from an object to be measured is used to measure fluorescence emitted when an object to be measured is irradiated with laser light, data on measured fluorescence has a certain degree of dispersion. Therefore, there is demand for a fluorescence measuring apparatus capable of reducing the dispersion of data on measured fluorescence in order to measure a fluorescence relaxation time etc. more accurately.

It is an object of the present invention to provide a fluorescence measuring apparatus and a fluorescence measuring method which make it possible to measure fluorescence emitted when an object to be measured is irradiated with laser light more accurately than before.

Solution to Problem

An apparatus for measuring fluorescence according to the present invention is an apparatus for measuring fluorescence emitted when an object to be measured is irradiated with laser light, the apparatus including: a laser light source that irradiates the object to be measured with laser light; a first light-receiving unit that receives scattered light emitted when the object to be measured is irradiated with the laser light; a second light-receiving unit that receives fluorescence emitted when the object to be measured is irradiated with the laser light; and a signal processing unit that assigns a weight to a signal of the fluorescence received by the second light-receiving unit depending on an intensity of the scattered light received by the first light-receiving unit.

Preferably, the signal processing unit determines a fluorescence lifetime based on a phase difference between a modulation signal for modulating an intensity of the laser light and the signal of the fluorescence received by the second light-receiving unit.

Preferably, the signal processing unit normalizes the intensity of the scattered light received by the first light-receiving unit and multiplies the signal of the fluorescence received by the second light-receiving unit by the normalized intensity of the scattered light.

A method for measuring fluorescence according to the present invention is a method for measuring fluorescence emitted when an object to be measured is irradiated with laser light, the method including: a step of irradiating the object to be measured with laser light; a first light-receiving step of receiving scattered light emitted when the object to be measured is irradiated with the laser light; a second light-receiving step of receiving fluorescence emitted when the object to be measured is irradiated with the laser light; and a signal processing step of assigning a weight to a signal of the fluorescence received in the second light-receiving step depending on an intensity of the scattered light received in the first light-receiving step.

Preferably, the signal processing step includes determining a fluorescence lifetime based on a phase difference between a modulation signal for modulating an intensity of the laser light and the signal of the fluorescence received in the second light-receiving step.

Preferably, the signal processing step includes normalizing the intensity of the scattered light received in the first light-receiving step, and multiplying the signal of the fluorescence received in the second light-receiving step by the normalized intensity of the scattered light.

Advantageous Effects of Invention

The fluorescence measuring apparatus and the fluorescence measuring method according to the present invention make it possible to measure fluorescence emitted when an object to be measured is irradiated with laser light more accurately than before.

DESCRIPTION OF EMBODIMENTS

Hereinbelow, a flow cytometer using a fluorescence measuring apparatus and a fluorescence measuring method according to the present invention will be described with reference to the following embodiment.

Embodiment

Structure of Flow Cytometer

Figure 1:
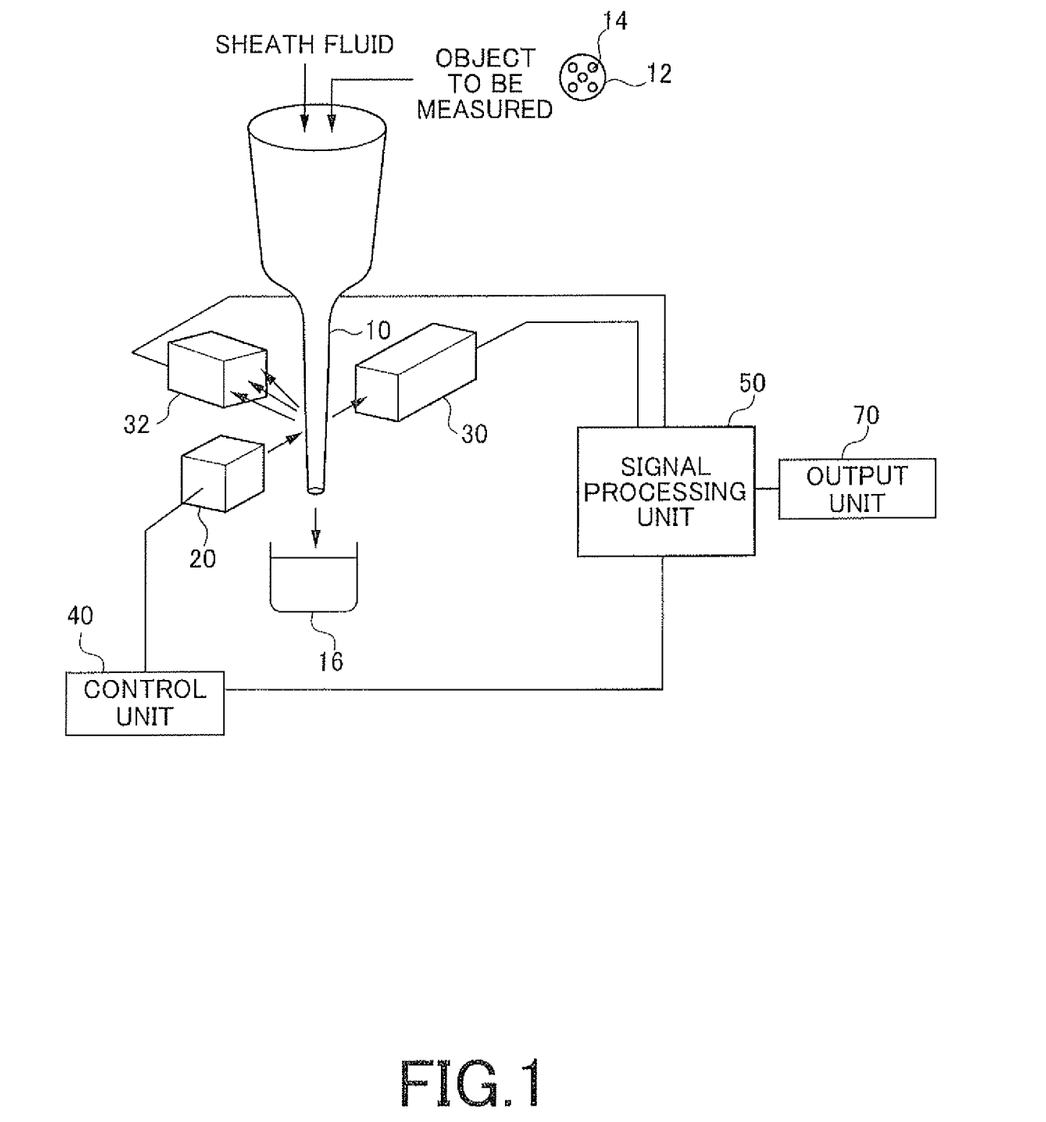
FIG. 1 is a schematic diagram illustrating one example of the structure of a flow cytometer according to an embodiment of the present invention.

First, the structure of a flow cytometer according to an embodiment of the present invention will be described with reference to FIG. 1. FIG. 1 is a schematic diagram illustrating one example of the structure of the flow cytometer according to this embodiment. The flow cytometer can acquire information about an object to be measured by irradiating the object to be measured with laser light and receiving fluorescence emitted from the object to be measured irradiated with the laser light.

As illustrated in FIG. 1, the flow cytometer according to this embodiment includes a flow cell 10, a laser light source 20, a first light-receiving unit 30, a second light-receiving unit 32, a control unit 40, a signal processing unit 50, and an output unit 70. Each of the components will be described in detail below.

Objects to be measured such as cells 12 are surrounded by a sheath fluid when flowing inside the flow cell 10. As will be described later, in order that the flow cytometer acquires information per object to be measured from fluorescence emitted when the object to be measured is irradiated with laser light emitted from the laser light source 20, the cells 12 are previously labeled with a fluorochrome 14. Examples of the fluorochrome 14 used include Cyan Fluorescent Protein (CFP) and Yellow Fluorescent Protein (YFP).

When flowing inside the flow cell 10, the objects to be measured are hydrodynamically focused by the surrounding sheath fluid into a narrow stream.

The laser light source 20 irradiates the object to be measured with laser light whose intensity is modulated at a predetermined frequency. As the laser light source 20, for example, a semiconductor laser may be used. The output power of the laser light is, for example, 5 to 100 mW. The wavelength of the laser light is, for example, 350 to 800 nm. The intensity of the laser light emitted from the laser light source 20 is modulated by a modulation signal outputted from the control unit 40 that will be described later.

The first light-receiving unit 30 and the laser light source 20 are arranged on opposite sides of a position where the flow cell 10 is irradiated with the laser light. The first light-receiving unit 30 receives forward-scattered light emitted when the object to be measured is irradiated with the laser light. The first light-receiving unit 30 has a photoelectric converter such as a photodiode. The first light-receiving unit 30 converts the received forward-scattered light into an electric signal.

The electric signal converted by the first light-receiving unit 30 is outputted to the signal processing unit 50 and used as a trigger signal that announces timing at which the object to be measured passes through the position where the flow cell 10 is irradiated with the laser light.

The second light-receiving unit 32 is arranged in a direction perpendicular to both a direction, in which the laser light emitted from the laser light source 20 travels, and a direction, in which the object to be measured flows inside the flow cell 10, with respect to the position where the flow cell 10 is irradiated with the laser light. The second light-receiving unit 32 receives fluorescence emitted when the object to be measured is irradiated with the laser light. The second light-receiving unit 32 has, for example, a photoelectric converter such as a photomultiplier tube. The second light-receiving unit 32 converts the received fluorescence into an electric signal (fluorescence signal).

The electric signal converted by the second light-receiving unit 32 is outputted to the signal processing unit 50 and used as information about the object to be measured that passes through the position where the flow cell 10 is irradiated with the laser light.

Figure 2:
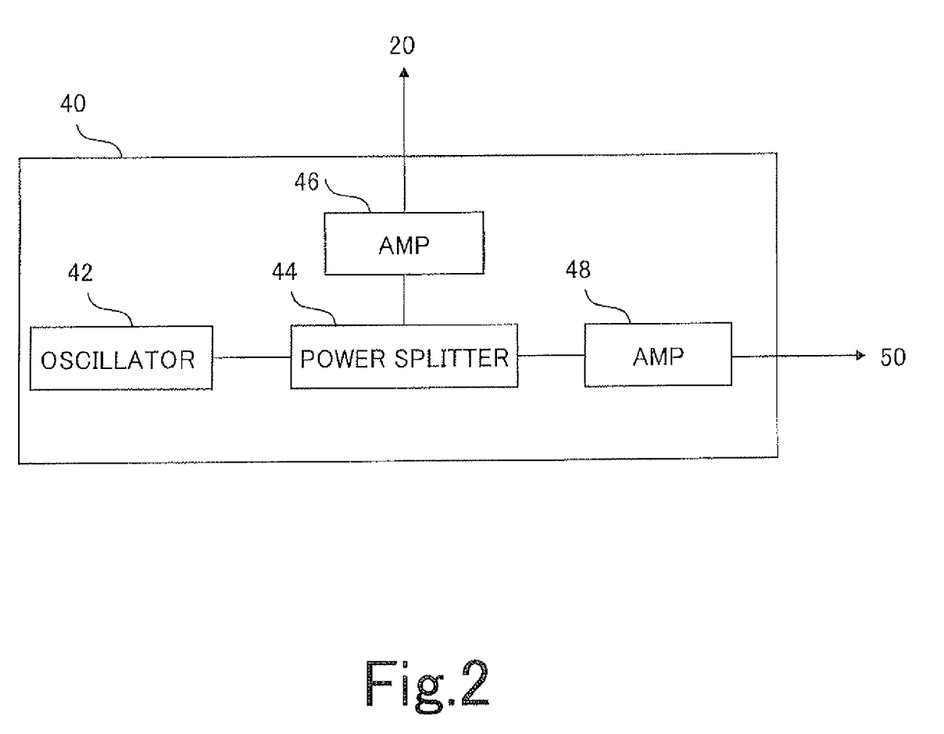
FIG. 2 is a diagram illustrating one example of a control unit illustrated in FIG. 1.

The control unit 40 will be described below. The control unit 40 controls the modulation frequency of the laser light emitted from the laser light source 20. The structure of the control unit 40 will be described with reference to FIG. 2. FIG. 2 is a diagram illustrating one example of the control unit 40. As illustrated in FIG. 2, the control unit 40 has an oscillator 42, a power splitter 44, and amplifiers 46 and 48.

The oscillator 42 outputs a sinusoidal signal with a predetermined frequency. The sinusoidal signal outputted from the oscillator 42 is used as a modulation signal for modulating the intensity of the laser light emitted from the laser light source 20. The frequency of the sinusoidal signal is, for example, 1 to 50 MHz.

The sinusoidal signal (modulation signal) with a predetermined frequency outputted from the oscillator 42 is distributed by the power splitter 44 to the two amplifiers 46 and 48. The modulation signal amplified by the amplifier 46 is outputted to the laser light source 20. The modulation signal amplified by the amplifier 48 is outputted to the signal processing unit 50. As will be described later, the reason why the modulation signal amplified by the amplifier 48 is outputted to the signal processing unit 50 is that it is used as a reference signal to detect a signal outputted from the second light-receiving unit 32.

Figure 3:
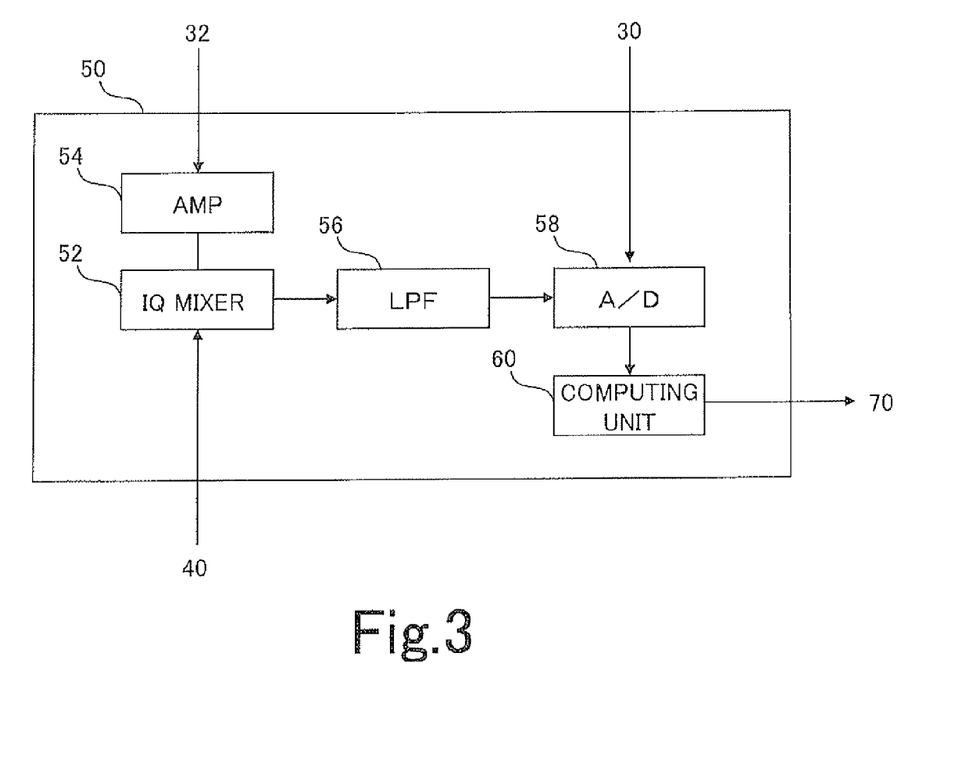
FIG. 3 is a diagram illustrating one example of a signal processing unit illustrated in FIG. 1.

The signal processing unit 50 will be described below. The signal processing unit 50 assigns a weight to a signal of the fluorescence received by the second light-receiving unit 32 depending on the intensity of the forward-scattered light received by the first light-receiving unit 30. Further, the signal processing unit 50 determines a fluorescence lifetime based on the phase difference between the modulation signal for modulating the intensity of the laser light and the signal of the fluorescence received by the second light-receiving unit 32. Here, the structure of the signal processing unit 50 will be described with reference to FIG. 3. FIG. 3 is a diagram illustrating one example of the signal processing unit 50. As illustrated in FIG. 3, the signal processing unit 50 has an IQ mixer 52, an amplifier 54, a low-pass filter 56, an A/D converter 58, and a computing unit 60.

The IQ mixer 52 receives, as an input, the fluorescence signal outputted from the second light-receiving unit 32 and amplified by the amplifier 54. Further, the IQ mixer 52 receives, as an input, the reference signal outputted from the amplifier 48 of the control unit 40.

The IQ mixer 52 multiplies the fluorescence signal and the reference signal to generate a signal containing a cos component of the fluorescence signal and a high-frequency component. Further, the IQ mixer 52 multiplies the fluorescence signal and a signal obtained by shifting the phase of the reference signal by 90° to generate a signal containing a sin component of the fluorescence signal and a high-frequency component. Based on these signals, the phase difference between the modulation signal (reference signal) and the fluorescence signal can be determined.

The high-frequency component of the signals generated by the IQ mixer 52 is removed by the low-pass filter 56. The signals from which the high-frequency component has been removed by the low-pass filter 56 are converted by the A/D converter 58 into digital signals ($\cos \theta$, $\sin \theta$ described later). Further, a signal of the forward-scattered light outputted from the first-light receiving unit 30 is converted by the A/D converter 58 into a digital signal.

The digital signals converted by the A/D converter 58 are outputted to the computing unit 60.

The computing unit 60 assigns a weight to a signal of the fluorescence received by the second light-receiving unit 32 (fluorescence signal) depending on the intensity of the forward-scattered light received by the first light-receiving unit 30. Further, the computing unit 60 normalizes the intensity of the forward-scattered light received by the first light-receiving unit 30 and multiplies the fluorescence signal by the normalized intensity of the forward-scattered light. Further, the computing unit 60 determines a fluorescence lifetime using the digital signals converted by the A/D converter 58. The processing performed by the computing unit 60 will be described in more detail later. The results of computations performed by the computing unit 60 are outputted to the output unit 70.

Referring to FIG. 1 again, the output unit 70 outputs information obtained by the signal processing unit 50. The output unit 70 is, for example, a display device or a printer. The output unit 70 outputs, for example, the fluorescence lifetime determined by the signal processing unit 50.

The above is the schematic structure of the flow cytometer according to this embodiment.

Signal Processing Flow

Hereinbelow, the flow of signal processing performed by the signal processing unit 50 will be described.

Figure 4A:
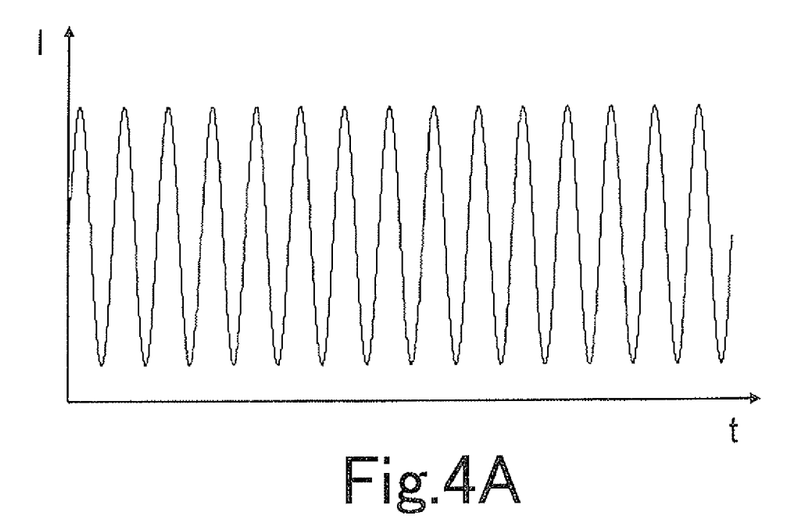
FIG. 4A is a graph illustrating one example of the temporal change of a reference signal and FIG. 4B is a graph illustrating one example of the temporal change of a fluorescence signal.

First, a modulation signal for modulating the intensity of the laser light is outputted as a reference signal from the control unit 40 to the signal processing unit 50. FIG. 4A is a graph illustrating one example of the temporal change of the reference signal inputted into the signal processing unit 50. The reference signal illustrated in FIG. 4A by way of example is a sinusoidal signal with a predetermined frequency.

Figure 4B:
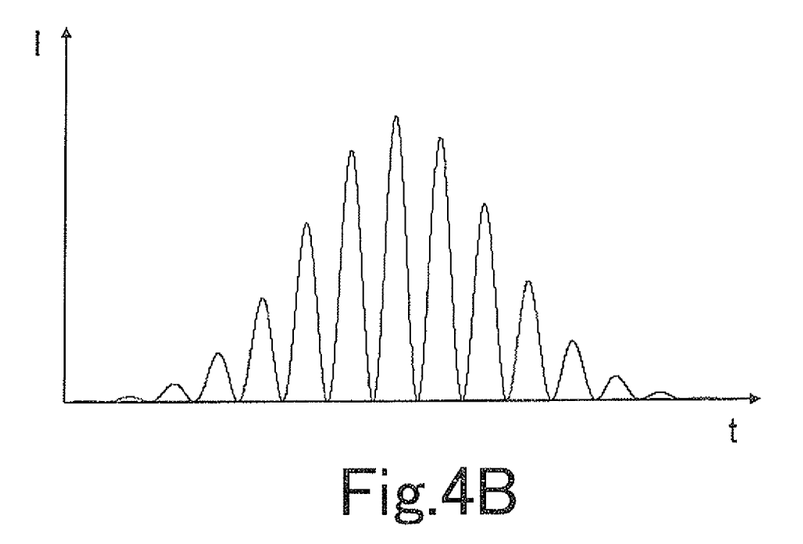

Further, fluorescence emitted when the object to be measured is irradiated with the laser light is received by the second light-receiving unit 32. FIG. 4B is a graph illustrating one example of the temporal change of a fluorescence signal outputted from the second light-receiving unit 32. The fluorescence signal has a phase difference $\theta$ with respect to the reference signal. Here, when the angular frequency of the modulation signal is represented by $\omega$ and the fluorescence lifetime of the object to be measured is represented by $\tau$, the fluorescence lifetime $\tau$ can be determined from the phase difference $\theta$ by the following formula (1):

[Formula 1]

$$\tan \theta = \omega \tau \tag{1}$$

Figure 5A:
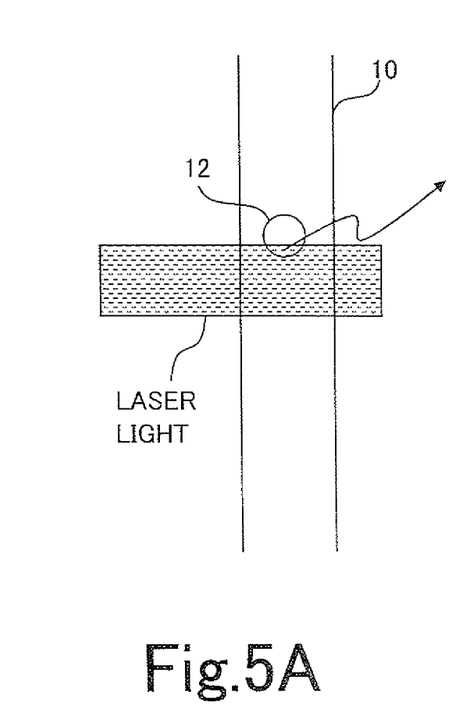
FIGS. 5A to 5C are diagrams illustrating how an object to be measured passes through a region irradiated with laser light.
Figure 5B:
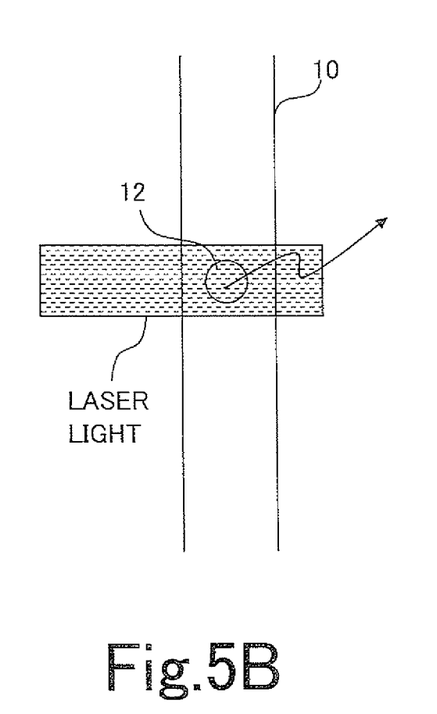
Figure 5C:
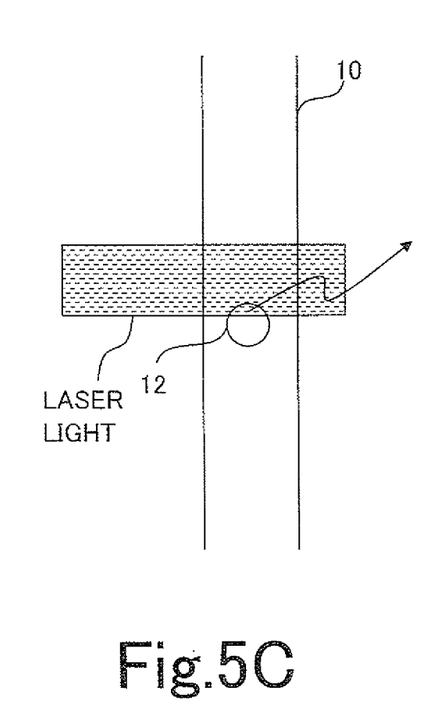

As illustrated in FIG. 4B, the amplitude of the fluorescence signal is not constant. The reason why the amplitude of the fluorescence signal changes will be described with reference to FIG. 5. FIG. 5 illustrates how the object to be measured such as the cell 12 passes through a region where the flow cell 10 is irradiated with the laser light. FIG. 5A is a diagram illustrating the instant when the object to be measured begins to enter the region irradiated with the laser light. FIG. 5B is a diagram illustrating the instant when the object to be measured is completely irradiated with the laser light. FIG. 5C is a diagram illustrating the instant when the object to be measured begins to exit the region irradiated with the laser light.

At any of the instants illustrated in FIGS. 5A to 5C, fluorescence is emitted from the object to be measured by irradiation with the laser light, but the intensity of the fluorescence is not constant. More specifically, the intensity of fluorescence emitted at the instant illustrated in FIG. 5B is greater than that of fluorescence emitted at the instant illustrated in FIG. 5A or 5C. For this reason, as illustrated in FIG. 4B, the amplitude of the fluorescence signal changes temporally.

Figure 6:
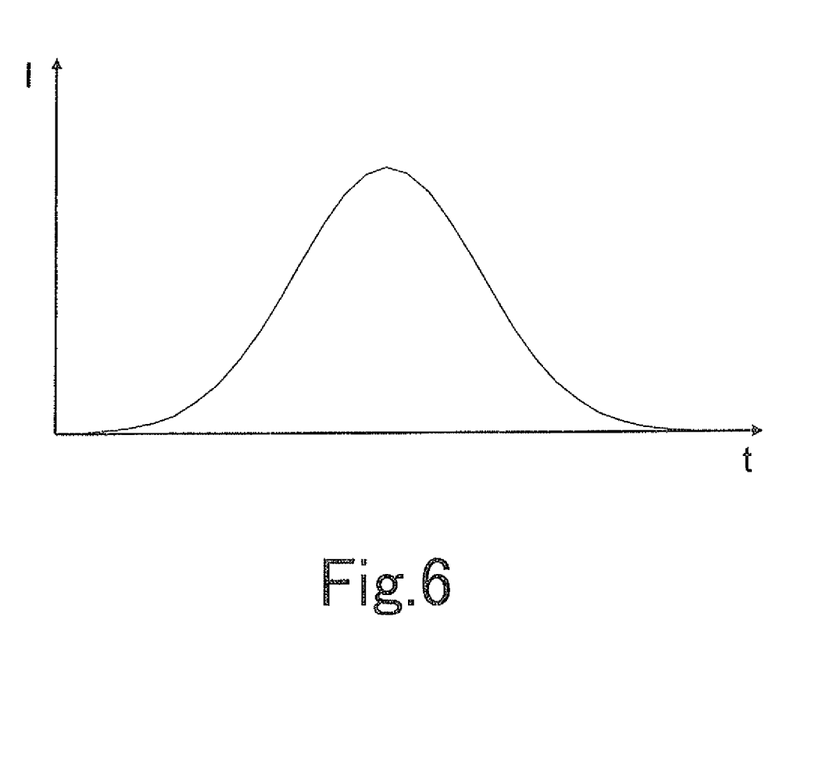
FIG. 6 is a graph illustrating one example of the temporal change of intensity of forward-scattered light.

Further, forward-scattered light emitted when the object to be measured is irradiated with the laser light is received by the first light-receiving unit 30. FIG. 6 is a graph illustrating one example of the temporal change of intensity of the forward-scattered light received by the first light-receiving unit 30. When the single object to be measured passes through the region where the flow cell 10 is irradiated with the laser light, one peak of forward-scattered light is measured. The instant when the intensity of the forward-scattered light is maximum corresponds to the above-described instant illustrated in FIG. 5B. A signal of the forward-scattered light is converted by the A/D converter 58 into a digital signal and inputted into the computing unit 60.

As described above, the frequency of the sinusoidal signal is, for example, 1 to 50 MHz. The time required for the object to be measured to pass through the position where the flow cell 10 is irradiated with the laser light is about 20 μs. Therefore, the signal illustrated in FIG. 4 generated when the single object to be measured passes through the position where the flow cell 10 is irradiated with the laser light actually has about 20 to 1000 cycles. The frequency of the signal illustrated in FIG. 4 is lower than it really is for convenience of description.

The IQ mixer 52 multiplies the fluorescence signal illustrated in FIG. 4B and the reference signal illustrated in FIG. 4A to generate a signal containing a cos component of the fluorescence signal and a high-frequency component. Then, the high-frequency component is removed by the low-pass filter 56. One example of the cos component of the fluorescence signal obtained by removing the high-frequency component is illustrated in FIG. 7A.

Further, the IQ mixer 52 multiplies the fluorescence signal illustrated in FIG. 4B and a signal obtained by shifting the phase of the reference signal illustrated in FIG. 4A by 90° to generate a signal containing a sin component of the fluorescence signal and a high-frequency component. Then, the high-frequency component is removed by the low-pass filter 56. One example of the sin component of the fluorescence signal obtained by removing the high-frequency component is illustrated in FIG. 7B.

Figure 7A:
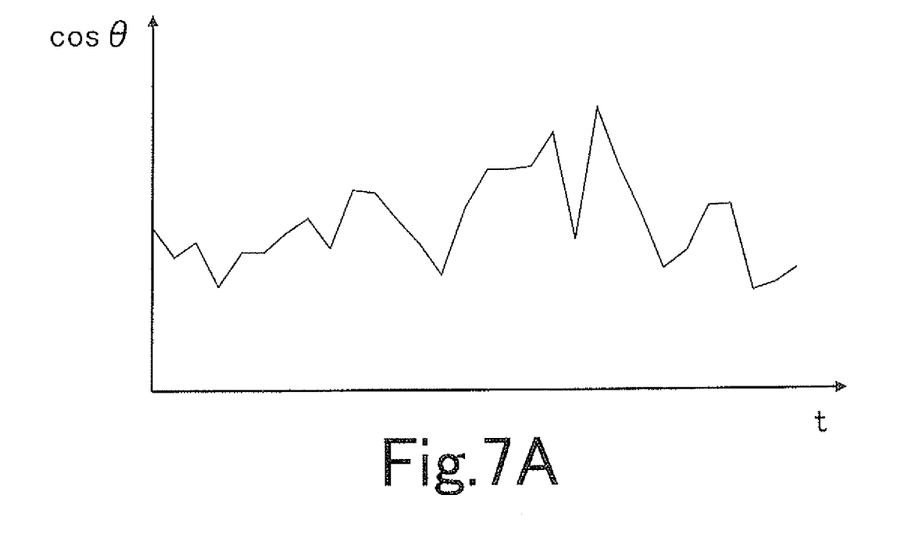
FIG. 7A is a graph illustrating one example of a cos component of the fluorescence signal and FIG. 7B is a graph illustrating one example of a sin component of the fluorescence signal.
Figure 7B:
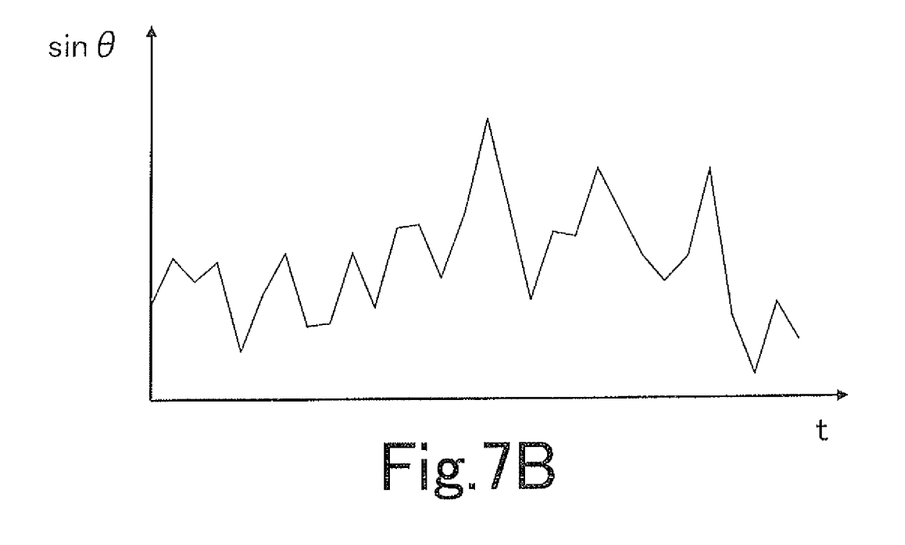
Figure 8A:
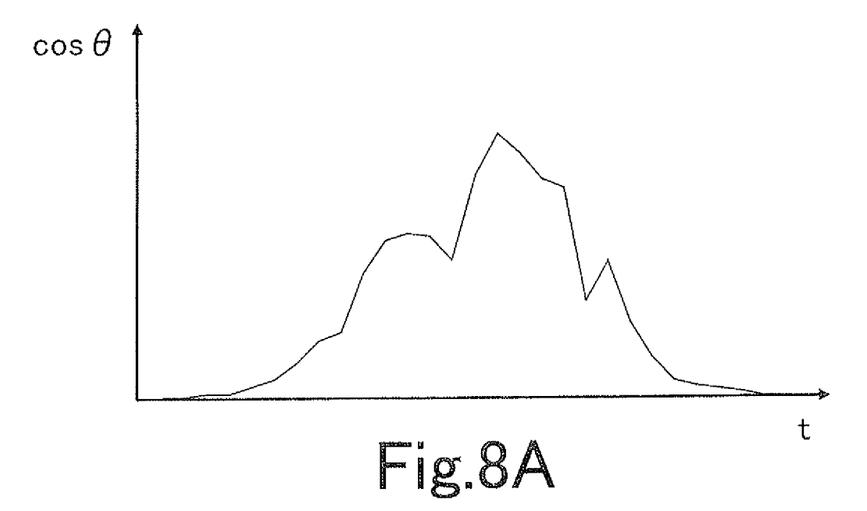
FIG. 8A is a graph illustrating one example of the cos component of the fluorescence signal multiplied by the normalized intensity of the forward-scattered light and FIG. 8B is a graph illustrating one example of the sin component of the fluorescence signal multiplied by the normalized intensity of the forward-scattered light.
Figure 8B:
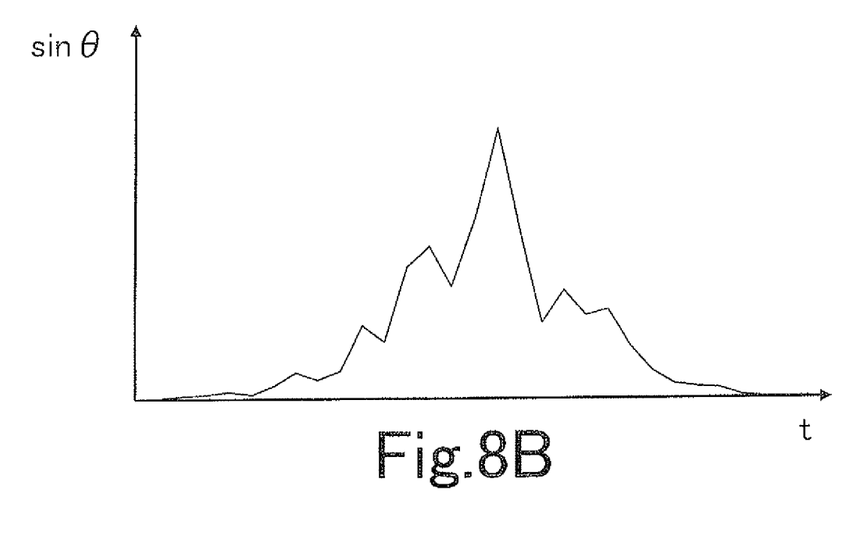

The computing unit 60 of this embodiment assigns a weight to each of the signals of cos and sin components of the fluorescence signal illustrated in FIGS. 7A and 7B depending on the intensity of the forward-scattered light illustrated in FIG. 6. More specifically, the computing unit 60 normalizes the intensity of the forward-scattered light illustrated in FIG. 6 so that the maximum value of the intensity of the forward-scattered light becomes 1, and multiplies each of the signals of cos and sin components of the fluorescence signal illustrated in FIGS. 7A and 7B by the normalized intensity of the forward-scattered light. The results obtained by multiplying the cos and sin components of the fluorescence signal illustrated in FIGS. 7A and 7B by the normalized intensity of the forward-scattered light are illustrated in FIGS. 8A and 8B. As illustrated in FIGS. 8A and 8B, the values of the fluorescence signal at portions where the intensity of the forward-scattered light is low are smaller than those illustrated in FIGS. 7A and 7B.

This is because fluorescence of high intensity emitted at the instant illustrated in FIG. 5B contains higher-accuracy information than fluorescence of low intensity emitted at the instant illustrated in FIG. 5A or 5C. Therefore, by multiplying the cos and sin components of the fluorescence signal by the normalized intensity of the forward-scattered light, it is possible to determine the phase difference θ using high-accuracy information.

Then, the computing unit 60 calculates the time average of cos component of the fluorescence signal illustrated in FIG. 5A and the time average of sin component of the fluorescence signal illustrated in FIG. 8B. The time-averaged cos and sin components of the fluorescence signal are plotted on a graph illustrated in FIG. 9. By performing the above-described signal processing on the single object to be measured, one point is plotted on the graph illustrated in FIG. 9.

The computing unit 60 plots the time-averaged cos and sin components of the fluorescence signals derived from the individual objects to be measured. Further, the computing unit 60 determines the phase difference of the fluorescence signal with respect to the reference signal from a plurality of plotted points of the time-averaged cos and sin components of the fluorescence signals. For example, the computing unit 60 can determine the phase difference θ of the fluorescence signal with respect to the reference signal from the inclination of a straight line obtained by approximating a plurality of plotted points on the graph illustrated in FIG. 9 by a straight line passing through the origin.

As has been described above, in the fluorescence measuring apparatus and the fluorescence measuring method according to this embodiment, a fluorescence signal is weighted in such a manner that a greater weight is assigned to a portion of fluorescence containing more accurate information depending on the intensity of forward-scattered light. This makes it possible to improve the measurement accuracy of fluorescence emitted when an object to be measured is irradiated with laser light.

Particularly, in the fluorescence measuring apparatus and the fluorescence measuring method according to this embodiment, weighting of a fluorescence signal is performed per object to be measured depending on the intensity of forward-scattered light. This makes it possible, even when objects to be measured are not constant in size, to improve the measurement accuracy of fluorescence emitted when the object to be measured is irradiated with laser light.

Comparative Example

Hereinbelow, a comparative example will be described to confirm the effect of the above-described embodiment.

Figure 10:
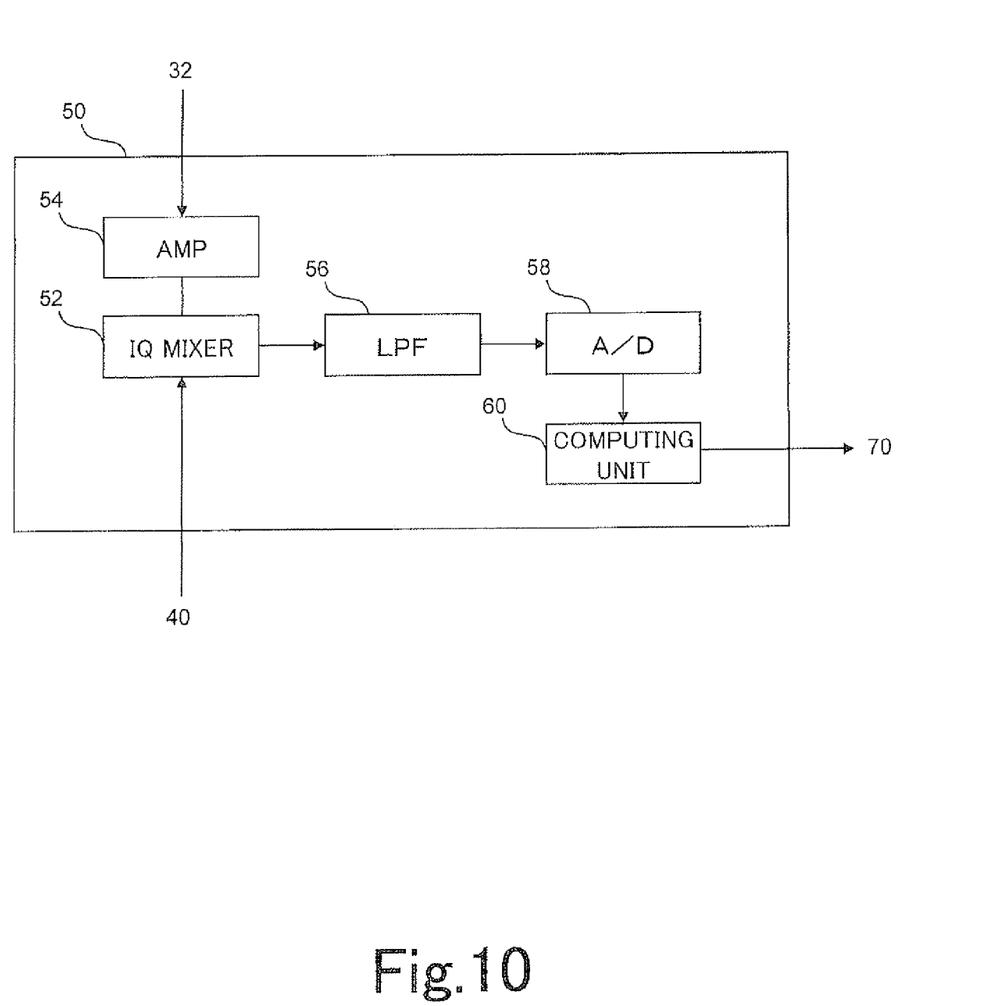
FIG. 10 is a diagram illustrating one example of a signal processing unit of a comparative example.

The structure of a flow cytometer of this comparative example is substantially the same as that of the above-described embodiment. However, the flow cytometer of this comparative example is different from the above-described embodiment in the structure of the signal processing unit 50. The signal processing unit 50 of this comparative example will be described below.

FIG. 10 is a diagram illustrating one example of the signal processing unit 50 of this comparative example. As illustrated in FIG. 10, the signal processing unit 50 of this comparative example has an IQ mixer 52, an amplifier 54, a low-pass filter 56, an A/D converter 58, and a computing unit 60.

The IQ mixer 52, the amplifier 54, the low-pass filter 56, and the A/D converter 58 have the same structure as those of the above-described embodiment, and therefore a description thereof will not be repeated. This comparative example is different from the above-described embodiment in that a signal of the forward-scattered light outputted from the first light-receiving unit 30 is not inputted into the signal processing unit 50.

The flow of signal processing performed by the signal processing unit 50 of this comparative example will be described below.

As has been described above with reference to FIG. 4A, a modulation signal for modulating the intensity of the laser light is outputted as a reference signal from the control unit 40 to the signal processing unit 50. Further, as has been described above with reference to FIG. 4B, fluorescence emitted when the object to be measured is irradiated with the laser light is received by the second light-receiving unit 32.

The IQ mixer 52 multiplies the fluorescence signal illustrated in FIG. 4B and the reference signal illustrated in FIG. 4A to generate a signal containing a cos component of the fluorescence signal and a high-frequency component. Then, as has been described above with reference to FIG. 7A, the high-frequency component is removed by the low-pass filter 56 to obtain the cos component of the fluorescence signal.

Further, the IQ mixer 52 multiplies the fluorescence signal illustrated in FIG. 4B and a signal obtained by shifting the phase of the reference signal illustrated in FIG. 4A by 90° to generate a signal containing a sin component of the fluorescence signal and a high-frequency component. Then, as has been described above with reference to FIG. 7B, the high-frequency component is removed by the low-pass filter 56 to obtain the sin component of the fluorescence signal.

The computing unit 60 of this comparative example calculates the time average of cos component of the fluorescence signal illustrated in FIG. 7A and the time average of sin component of the fluorescence signal illustrated in FIG. 7B. The time-averaged cos and sin components of the fluorescence signal are plotted on a graph illustrated in FIG. 11. Further, the computing unit 60 determines the phase difference of the fluorescence signal with respect to the reference signal from a plurality of plotted points of time-averaged cos and sin components of the fluorescence signals.

Figure 9:
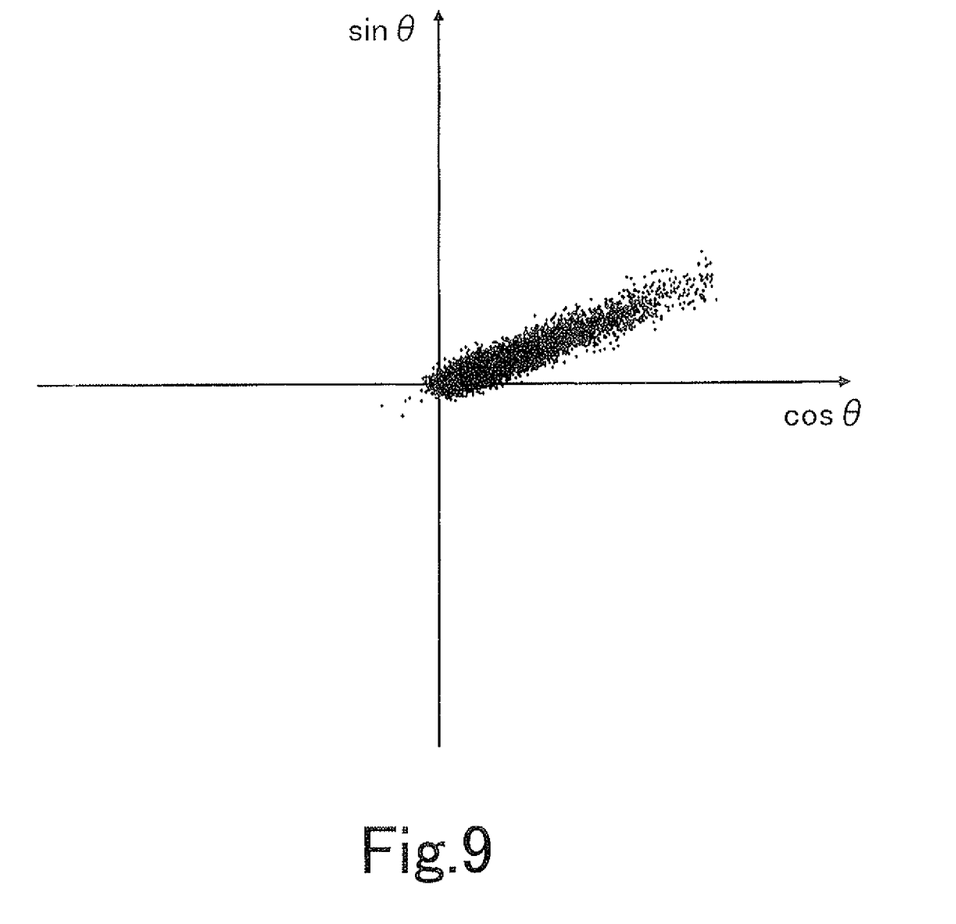
FIG. 9 is a graph illustrating one example of the phase difference of the fluorescence signal with respect to the reference signal.
Figure 11:
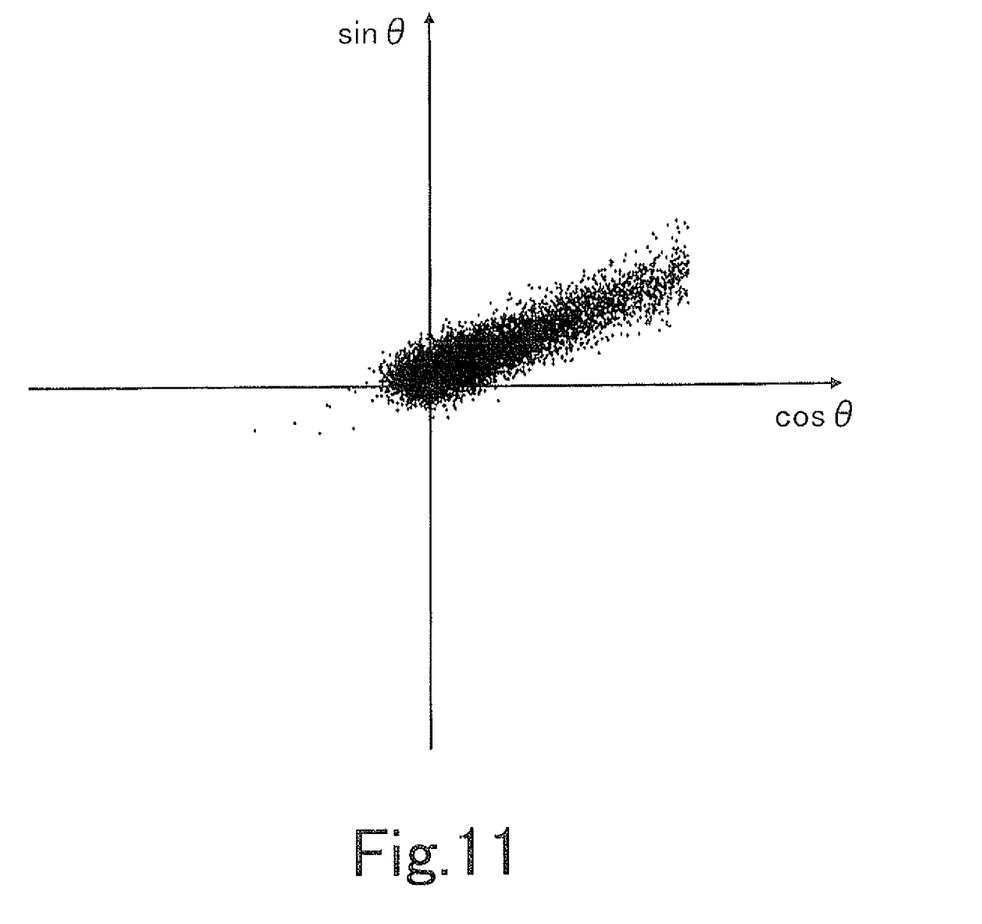
FIG. 11 is a graph illustrating one example of the phase difference of a fluorescence signal with respect to a reference signal in the comparative example.

A comparison between the plot illustrated in FIG. 9 obtained by the above-described embodiment and the plot illustrated in FIG. 11 obtained by this comparative example shows that the dispersion of the plotted points is smaller in the plot of the embodiment than in the plot of this comparative example. For example, a standard deviation determined from the dispersion of the phase difference θ plotted in FIG. 11 is 0.79 (rad), whereas a standard deviation determined from the dispersion of the phase difference θ plotted in FIG. 9 is 0.71 (rad). This is because, in the fluorescence measuring apparatus and the fluorescence measuring method according to the embodiment, a fluorescence signal is weighted in such a manner that a greater weight is assigned to a portion of fluorescence containing more accurate information depending on the intensity of forward-scattered light. Therefore, the fluorescence measuring apparatus and the fluorescence measuring method according to the embodiment make it possible to measure a fluorescence lifetime more accurately.

Although the fluorescence measuring apparatus and the fluorescence measuring method according to the present invention have been described above in detail, the present invention is not limited to the above embodiment. Further, it is apparent that various modifications and changes may be made without departing from the scope of the present invention.

REFERENCE SIGNS LIST 10 flow cell
12 cell
14 fluorochrome
16 container
20 laser light source
30 first light-receiving unit
32 second light-receiving unit
40 control unit
42 oscillator
44 power splitter
46, 48 amplifier
50 signal processing unit
52 IQ mixer
54 amplifier
56 low-pass filter
58 A/D converter
60 computing unit
70 output unit

The invention claimed is:

1. An apparatus for measuring fluorescence emitted when an object to be measured is irradiated with laser light, the apparatus comprising:
a laser light source that irradiates the object to be measured with laser light whose intensity is modulated at a frequency by a modulation signal;
a first light-receiving unit that receives scattered light emitted when the object to be measured is irradiated with the laser light;
a second light-receiving unit that receives fluorescence emitted when the object to be measured is irradiated with the laser light; and
a signal processing unit that assigns a greater weight to a first signal component of the fluorescence in phase with the modulation signal and a second signal component of the fluorescence whose phase is shifted from the modulation signal by 90 degrees, as an intensity of the scattered light gets higher, the first signal component and the second signal component being obtained from a signal of the fluorescence received by the second light-receiving unit.

2. The fluorescence measuring apparatus according to claim 1, wherein the signal processing unit determines a fluorescence lifetime based on a phase difference between a modulation signal for modulating an intensity of the laser light and the signal of the fluorescence received by the second light-receiving unit.

3. The fluorescence measuring apparatus according to claim 1, wherein the signal processing unit normalizes the intensity of the scattered light received by the first light-receiving unit and multiplies the signal of the fluorescence received by the second light-receiving unit by the normalized intensity of the scattered light.

4. A method for measuring fluorescence emitted when an object to be measured is irradiated with laser light, the method comprising:
a step of irradiating the object to be measured with laser light whose intensity is modulated at a frequency by a modulation signal;
a first light-receiving step of receiving scattered light emitted when the object to be measured is irradiated with the laser light;
a second light-receiving step of receiving fluorescence emitted when the object to be measured is irradiated with the laser light; and
a signal processing step of assigning a greater weight to a first signal component of the fluorescence in phase with the modulation signal and a second signal component of the fluorescence whose phase is shifted from the modulation signal by 90 degrees, as the intensity of forward-scattered light gets higher, the first signal component and the second signal component being obtained from a signal of the fluorescence received in the second light-receiving step.

5. The fluorescence measuring method according to claim 4, wherein the signal processing step comprises determining a fluorescence lifetime based on a phase difference between a modulation signal for modulating an intensity of the laser light and the signal of the fluorescence received in the second light-receiving step.

6. The fluorescence measuring method according to claim 4, wherein the signal processing step comprises normalizing the intensity of the scattered light received in the first light-receiving step, and multiplying the signal of the fluorescence received in the second light-receiving step by the normalized intensity of the scattered light.

7. The apparatus according to claim 1, further comprising a flow cell in which the object to be measured flows throughout a region irradiated with the laser light;
the signal processing unit being configured to calculate time averages of the weighted first signal component and the weighted second signal component from a time when the object to be measured begins to enter the region to a time when the object to be measured begins to exit the region, to determine a phase difference between the modulation signal and the signal of the fluorescence by using the calculated time averages.

8. The method according to claim 4, wherein the object to be measured flows through a region irradiated with the laser light in the step of irradiating the object to be measured with laser light, and
the signal processing step includes calculating time averages of the weighted first signal component and the weighted second signal component from a time when the object to be measured begins to enter the region to a time when the object to be measured begins to exit the region, to determine a phase difference between the modulation signal and the signal of the fluorescence by using the calculated time averages.

* * * * *